United States Patent [19]

Greenwood et al.

[11] 4,327,327
[45] Apr. 27, 1982

[54] ALL-ANGLE GRADIENT MAGNETOMETER

[75] Inventors: Ivan A. Greenwood, Stamford, Conn.; James H. Simpson, Katonah, N.Y.

[73] Assignee: The Singer Company, Little Falls, N.J.

[21] Appl. No.: 156,709

[22] Filed: Jun. 5, 1980

[51] Int. Cl.³ ............................................ G01N 27/00
[52] U.S. Cl. ...................................... 324/304; 324/302
[58] Field of Search ............... 324/300, 301, 302, 304, 324/305, 316

[56] References Cited

U.S. PATENT DOCUMENTS 3,863,144  1/1975  Simpson ............................. 324/301

*Primary Examiner*—Michael J. Tokar

*Attorney, Agent, or Firm*—John C. Altmiller; Thomas W. Kennedy

[57] ABSTRACT

In order to provide an all-angle gradient magnetometer, first and second magnetic resonance cells are mounted to a common base and separated by a predetermined distance. Circularly polarized pumping light is passed through the two cells orthogonally. Mixed with the circularly polarized pumping light is readout light which is linearly polarized. At the output of the cells appropriate filters are provided to filter out the pumping light whereafter the modulated readout light is detected in push-pull manner and fed back to modulate the pumping beams and at the same time fed to signal processing means to permit detecting phase differences between the outputs of the separated cells.

14 Claims, 2 Drawing Figures

ALL-ANGLE GRADIENT MAGNETOMETER

BACKGROUND OF THE INVENTION

This invention relates to magnetometers in general and more particularly to a high sensity gradient magnetometer which is operable at all angles with respect to the magnetic field being measured.

A high sensitivity microgradient magnetometer utilizing two interconnected magnetic resonance spin generators on a common base is described in U.S. Pat. No. 3,863,144. In the device disclosed therein, magnetic resonance cells are pumped by a common pumping means which is divided by beam splitters. A seperate readout lamp is utilized, coupled through a beam divider, to detect differences, caused by gradients in the scalar magnitude of the earth's magnetic field.

The major disadvantage of a magnetometer such as that disclosed in the aforementioned patent is that it is not operable for all orientations relative to the magnetic field being measured. Typically, a magnetometer of this nature will be mounted in an aircraft for use in detecting bodies on the surface of the earth which distort the earth's magnetic field. A typical example is the use in marine vessel detection or use in prospecting to find mineral deposits. To be a more useful device in such an application, the magnetometer should operate over all angles, that is, on all headings and at all magnetic latitudes. However, a magnetometer of this nature is not sensitive if the magnetic field lies along the direction of the readout beams, and may be in error when the magnetic field does not lie along the direction of the pump beams.

Thus, the need for an all-angle gradient magnetometer of this nature becomes evident.

SUMMARY OF THE INVENTION

It is the object of the present invention to provide an all-angle, high sensitivity gradient magnetometer utilizing magnetic resonant spin generators.

Such is accomplished in a system which, like the system of the aforementioned patent, utilizes a pair of magnetic resonant cells. However, to accomplish an all angle capability, the system of the present invention differs therefrom. Whereas the system of U.S. Pat. No. 3,863,144 utilized pumping with unmodulated light having a component along the magnetic field, pumping is accomplished in the system of the present invention with a circularly polarized cross beam modulated at the Larmor or precession frequency. In the system of the present invention both the pump beam and readout beam share the same path through the resonance cell. Thus, light from the pumping lamp is modulated, converted to circularly polarized light, mixed with linearly polarized light from a readout lamp, and passes through a cell. Through necessary beam dividers the pumping radiation and readout radiation are supplied to the two cells which are separated from each other but mounted on a common base to eliminate gyroscopic effects. As an alternative to the use of a modulated pump lamp, separate modulated lasers may be used. The element used in the magnetic resonance cell may be any of the alkali metals or other elements suitable for optically pumped and optically readout magnetic resonance such as selected isotopes of mercury or metastable helium. A preferred material is the alkali metal cesium having a D1 line at 894.3 nanometers and a D2 line at 852.1 nanometers. The pumping lamp is operated at the one D line and the readout lamp near the other D line. On the output side of the cell a filter removes the pump beam light and permits only the modulation impressed on the orientation of the plane of polarization of the readout beam by the precessing moment (Faraday effect) to be recovered by a polarizing beam splitter and photodetectors operating in push-pull. The a-c signal derived at the output is fed back to drive the modulator for the pump beam to complete a spin generator loop, causing oscillation to continue at the Larmor frequency.

In order to obtain all-angle operation, since the spin generator operation will fail completely if the magnetic field lies along the direction of the optical beams, but since operation is possible if there is some non-zero angle between the magnetic field and direction of beams, a second set of beams and other components is introduced with its axis perpendicular to the axis of the first set of beams. Although optimum operation is where the beam is at 90° to the magnetic field, operation is possible at any non-zero angle. Thus, both spin generator paths are operable under most conditions. A simple decision circuit can be used to select the most favorable case. It is also possible under some conditions to combine both outputs.

The component along the instrument axis of the gradient of the magnitude of the earth's magnetic field, B, is obtained using high precision differential phase measurements of the spin generator outputs associated with the two cells. The rate of change of differential phase is a measure of the field gradient. A number of different phase comparators can be used for this purpose. A preferred type of device is that disclosed in co-pending application Ser. No. 931,702 assigned to the same assignee as the present invention.

DETAILED DESCRIPTION OF THE INVENTION

Figure 1:
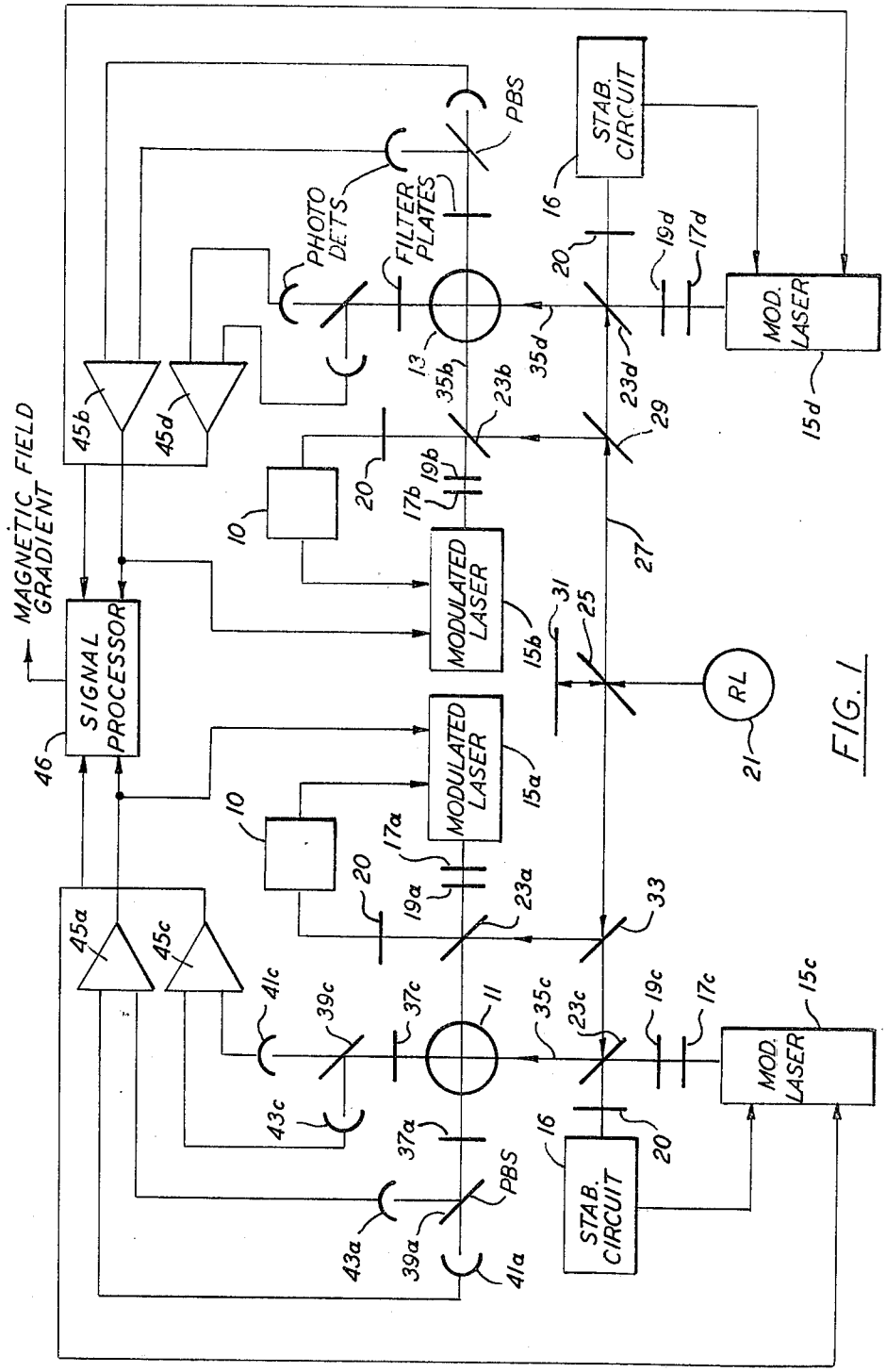
FIG. 1 is schematic-block diagram of a first embodiment of the present invention utilizing modulated lasers.

As illustrated by FIG. 1, two magnetic resonance cells 11 and 13 are supported on a common base spaced from each other a distance of one meter, for example. The cells can contain any of a number of elements adapted for optically pumped and optically readout magnetic resonance. An element which has been found particularly useful is cesium vapor which has a D1 line at 894.3 nanometers and a D2 line at 852.1 nanometers. In the embodiment illustrated in FIG. 1, there are provided four separate lasers designated respectively, 15a, 15b, 15c and 15d. For example, a diode laser may be used. Lasers 15a–15d provide the pumping energy through the cells 11 and 13. They must be operated at an optical frequency corresponding to a resonance line of the element used, such as one of the D lines of the alkali metals. Each laser is provided with a stabilizing circuit 16 to maintain this frequency. Alternatively, stabilized lasers may be used. Depending on the bandwidth obtainable from these lasers, the output from each will first be passed through an optical filter of a frequency corresponding to the selected D line, 17a, 17b, 17c or 17d respectively. However, if the laser has a very stable output and extremely narrow bandwidth, the filters may be eliminated. Light from each of the lasers next passes through a quarter wave plate 19a, 19b, 19c or 19d, to circularly polarize the light therefrom. Again, if a laser which provides circularly polarized light in its output is used, these quarter wave plates can be eliminated. In the remaining discussion, only the output from the modulated laser 15a, and its passage through the resonance cell 11, will be discussed in detail. Operation with each of the other lasers 15b, 15c and 15d, is the same.

The circularly polarized light leaving the quarter wave plate 19a is mixed with linearly polarized light from a readout lamp 21, operating near the frequency of the other D line at a beam splitter and beam combiner 23a. Beam splitter 23a also directs some of the light from the laser through a filter 20 to a detector at stabilizing circuit 16 which then provides feedback to maintain the desired frequency. The beam splitter and combiner may comprise an optical, e.g., glass, surface silvered on both sides with a plurality of opposed strips so as to alternately reflect and transmit in adjacent zones. Light from the readout lamp 21 is directed toward a beam splitter 25. A certain amount of the light is reflected in a path 27, to a beam splitter 29. Here a portion of the light is reflected to be mixed with the polarized light at the beam splitter 23b. Another portion of the light passes through the beam splitter 29 to be mixed with the circularly polarized light at the beam splitter 23d. Beam splitter 29 is a polarizing beam splitter, e.g., a stack of glass plates at the Brewster angle, and transmits and reflects opposite senses of linear polarization. Other types of linear polarizing devices such as a dielectric layer beam splitter may also be used. Another portion of the radiation from the readout lamp 21 passes through the beam splitter 25 and is reflected from a mirror 31. It is directed back to the other side of the beam splitter 25 from which it is reflected to another polarizing beam splitter 33. Light from this beam splitter is then directed to the beam splitter 23a and the beam splitter 23c for mixing with the circularly polarized pumping light from the modulated lasers 15a and 15c respectively. Thus, the beam 35 from the beam splitter 23a, for example, now contains a mixture of linearly polarized light from the readout lamp at one of the D lines, for example, the D2 line, mixed with circularly polarized light from the modulated laser 15a at the D1 line, for example. In conventional fashion, the modulated pumping radiation is used to excite resonance in the elements in the resonant cell 11. The polarization angle of the linearly polarized readout light becomes modulated by the precessing moments within the cell, and thus, is an indication of the phase of the precessing moments. Light coming out through the cell 11 is then passes through an optical filter 37a which acts to pass the readout light and to filter out the pumping light. Polarization angle modulated readout light then is directed to a polarizing beam splitter 39a oriented to equally divide the incoming light in the absence of polarization modulation. As indicated above, a polarizing beam splitter will pass light with one direction of polarization and will reflect light with the opposite sense of linear polarization. The light transmitted, and the light reflected are thus amplitude modulated and are provided as inputs to first and second photodetectors 41a and 43a. The fact that the a-c inputs to these two photodetectors are 180° out of phase, then permits operating in a push-pull mode, these outputs being coupled into an amplifier 45a. Common mode intensity modulation due, for example, to leakage of modulated pump light through filter 37a is rejected. The output of the amplifier 45a is provided as a modulating input to the modulated laser 15a to close the loop and maintain precession at the Larmor frequency.

Operation over each of the other paths, i.e., the paths 35b, 35c and 35d is the same as described, with the final outputs being provided to the amplifiers 45a, 45b, 45c and 45d. Each amplifier provides a feedback to its respective modulated laser to maintain the loop in operation. The outputs of the amplifiers are also used as the output from which the phase difference is determined. Typically, for example, if the magnetic field is somewhere along the direction of the lines 35c and 35d, then the outputs of the amplifiers 45a and 45b will be used. On the other hand, if the magnetic field is closer to being parallel to the lines 35a and 35b, the outputs of the amplifiers 45c and 45d will be used. The outputs are supplied to signal processor 46 the output of which is the magnetic field gradient. As noted above, processing of the signals to determine the phase difference can be carried out by apparatus such as that disclosed in copending application Ser. No. 931,702.

The embodiments just discussed has as a major advantage the use of lasers as the pumping light source. Lasers are readily available and easily modulated. The major disadvantage of this embodiment is that at least two separate lasers are used during any stage of measurement. They can thus have outputs which are variable and this can introduce errors.

Figure 2:
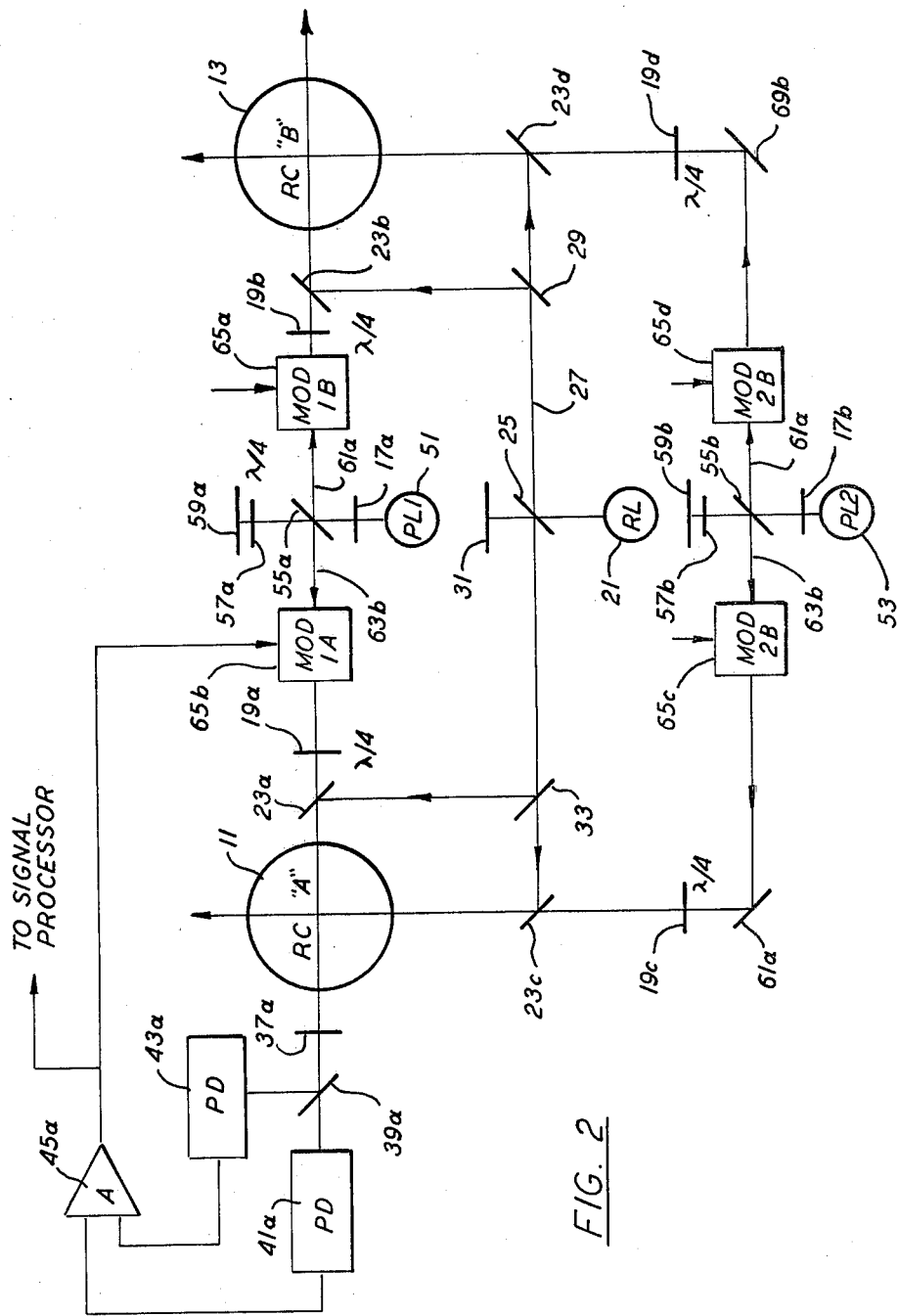
FIG. 2 is a similar diagram of an embodiment of the present invention utilizing first and second common pumping lamps for operation along the two orthogonal axes.

The embodiment of FIG. 2 overcomes this disadvantage by using a common puming light source for each of the two pumping beams. In FIG. 2, those elements which are the same as FIG. 1, are given the same reference numerals. Also, it should be noted that only one output arrangement, i.e., filter plate 37a, polarizing beam splitter 39a, photodetectors 41a and 43a, and amplifier 45a are shown. Similar elements are, of course, provided for the other paths, as they are in FIG. 1, but are not shown for the sake of clarity.

As will be evident from examination of FIG. 2, the majority of the elements are the same as in FIG. 1. The primary difference is that instead of having the lasers 15a–d there is a first pumping light source 51 and a second pumping light source 53. The output of the pumping light source 51 is directed through a filter 17a which will be at the first D line. Thereafter, it passes through a polarizing beam splitter 55a with a portion of the light reflected and another portion passing through. The light that passes through then goes through a quarter wave plate 57a and is reflected from a mirror 59a. The light is reflected back through the quarter wave plate 57a and reflects off the polarizing beam splitter 55a. Use of the quarter wave plate 57a insures proper polarization, i.e., the beam 61a directed to the right and the beam 63a directed to the left will have the same type of polarization after passing through this arrangement. The beam 61a enters a modulator 63a and the beam 63b, a modulator 63b. Modulators 65a and 65b can be, for example, Pockel cells. From this point on, the paths of the beams are exactly as described above in connection with FIG. 1. Light from the pumping lamp 53, after passing through the filter plate 17b, follows a path similar to that of the light from pumping lamp 51. It too is partially reflected and partially passed through a polarizing beam splitter 55b. The transmitted light then passes through a quarter wave plate 7b and is reflected by a mirror 59b back through the quarter wave plate 57b after which it is reflected to the left by the polarizing beam splitter 55b. The beams 61b and 63b enter the modulators 65c and 65d, respectively, where they are modulated. Again, the arrangement is as shown in FIG. 1, except that there are additional mirrors, the mirrors 69a and 69b, to reflect the light from the quarter wave plates 19c and 19d to the beam splitters 23c and 23d. Such was not necessary previously since separate sources were used. In the arrangement of FIG. 2, the detected output is fed to the respective modulators 65a, b, c, and d, to again close the loop. Also, as indicated and as described in connection with FIG. 1, these outputs are also provided to signal processing means.

It should be noted that lasers may be used in place of the lamps of FIG. 2.

Furthermore, although disclosed as a gradient magnetometer, it will be recognized that by using only one cell and its associated pumping and read out sources, an all angle magnetometer can be provided.

In addition to cesium, the vapor of any of the other akalai metals, particularly rubidium, may be used in the cells 11 and 13. Also useful for this purpose are two mercury isotopes 199 and 201. In such a case one of the sources pumping, includes one of the isotopes 199, 201, 204 or 198 and the other readout, a different isotope not having overlapping hyperpine components, e.g., mercury 208.

What is claimed is:

1. An all angle gradient magnetometer comprising:
    (a) first and second magnetic resonance cells containing an element adapted for optically pumped and optically readout magnetic resonance rigidly mounted to a common base and separated by a predetermined distance;
    (b) means for generating circularly polarized first, second, third and fourth modulated beams of optical radiation at an optical pumping frequency co-acting with the said resonance element, said means accepting first, second, third and fourth modulating inputs;
    (c) means for directing said first and second beams through said first cell at right angles to each other;
    (d) means for directing said third and fourth beams through said second cell at right angle to each other;
    (e) a common readout source of light at an optical readout frequency coacting with the said resonance element frequency;
    (f) means for mixing light from said readout source with each of said first, second, third and fourth beams before said beams pass through said first and second cells;
    (g) means to simultaneously reject light at the pumping frequency and to detect the light from the readout source in each of said beams after passing through said cells and to provide modulating inputs to said means for generating.
    (h) signal processing means receiving inputs from said means to detect and providing the magnetic field gradient as an output.

2. Apparatus according to claim 1 wherein said means to reject and detect comprise means to reject amplitude modulation and detect phase modulation of said readout source.

3. Apparatus according to claim 2 wherein said means to reject amplitude modulation and detect phase modulation comprise first, second, third and fourth filters interposed in said first, second, third and fourth beams respectively, after said beams pass through said cells, adapted to pass only the light from said readout source; and a first, second, third and fourth push-pull detectors for detecting said readout source.

4. Apparatus according to claim 3 wherein said first, second, third and fourth push-pull detectors comprise:
    (a) first, second, third and fourth polarizing beam splitters disposed respectively to intercept said first, second, third and fourth beams after passing through said first, second, third and fourth filters respectively, said beam splitters each transmitting approximately half the light incident thereon and reflecting the remainder;
    (b) a pair of photodetectors for each beam splitter arranged to intercept, respectively, transmitted and reflected light from said beam splitters; and
    (c) first, second, third, and fourth amplifiers receiving as differential inputs the outputs of the pairs of detectors associated with each of said beam splitters, the outputs of said amplifiers providing the modulating inputs to said means for generating.

5. Apparatus according to claim 4 wherein said means to generate comprise means to supply first, second, third and fourth modulated beams and first, second, third and fourth quarter wave plates interposed in said respective modulated beams.

6. Apparatus according to claim 5 wherein said means to supply comprise first, second, third and fourth modulated lasers.

7. An apparatus according to claim 5 and further including a filter at said optical pumping frequency interposed between each of said means to supply and a respective quarter wave plate.

8. Apparatus according to claim 5 wherein said means to supply comprise:
    (a) a first pumping light source;
    (b) means to split radiation from said first light source into two beams;
    (c) a first modulator having one of said two beams as an input and providing said first modulated beam at its ouput;
    (d) a second modulator having the other of said two beams as an input and providing said third beam at its output;
    (e) a second pumping light source;
    (f) means to split radiation from said second light source into another two beams;
    (g) a third modulator having one of said another two beams as an input and providing said second modulated beam at its output;
    (h) a fourth modulator having the other of said another two beams as an input and providing said fourth beam at its output.

9. An apparatus according to claim 8 and further including a filter at said optical pumping frequency in the path of each of said first and second pumping light sources.

10. An apparatus according to claim 8 wherein said first, second, third and fourth modulators comprise Pockel cells.

11. An apparatus according to claim 1 wherein said first and second magnetic resonance cells comprise cells containing vapor of any one of the alkali metals and wherein said means for generating circularly polarized beams generates beams which are at the frequency of one D line of said alkali metal and wherein said means for generating a common readout source of light generates light at the other D line of said alkali metal.

12. Apparatus according to claim 11 wherein said alkali metal is selected from the group consisting of cesium and rubidium.

13. Apparatus according to claim 1 wherein said first and second magnetic resonance cells comprise cells containing the mercury isotope 199, and wherein said source of pumping radiation includes at least one of mercurcy 199, 201 and 204, and said source of readout radiation is at least one of mercury 198, 200, 202 and 204, said readout radiation being from different isotopes than said pumping radiation.

14. An all angle magnetometer comprising:
- (a) a resonant cell containing an element adapted for optically pumped and optically readout magnetic resonance rigidly mounted to a base;
- (b) means for generating circularly polarized first and second beams of optical pumping radiation at an optical pumping frequency coacting with said resonance element said means accepting first and second modulating inputs;
- (c) means for directing said first and second beam through said cell at right angles to each other;
- (d) a readout source of light at an optical readout frequency coacting with said resonance element;
- (e) means for mixing light from said readout source with each of said first and second beams before said beams pass through said cell;
- (f) means to simultaneously reject light at the pumping frequency and to detect light from the readout source in each of said beams after passing through said cells and to provide said modulating inputs for said means generating; and
- (g) signal processing means receiving an input from said means to detect and providing an output representing magnetic field intensity.

* * * * *